US005173432A

United States Patent [19]
Lefkowitz et al.

[11] Patent Number: 5,173,432
[45] Date of Patent: * Dec. 22, 1992

[54] APPARATUS AND METHOD FOR MEASURING THE CONCENTRATION OR PARTIAL PRESSURE OF OXYGEN

[75] Inventors: Steven M. Lefkowitz, Walnut Creek, Calif.; Steven P. Webb; Michael S. Paquette, both of Midland, Mich.

[73] Assignee: The Dow Chemical Company, Midland, Mich.

[*] Notice: The portion of the term of this patent subsequent to Feb. 19, 2008 has been disclaimed.

[21] Appl. No.: 257,362

[22] Filed: Oct. 13, 1988

Related U.S. Application Data

[63] Continuation-in-part of Ser. No. 133,594, Dec. 14, 1987, Pat. No. 4,994,396.

[51] Int. Cl.[5] ............................................. G01N 33/26
[52] U.S. Cl. ............................... 436/138; 128/633; 128/634; 128/635; 128/664; 128/665; 128/666; 250/458.1; 250/459.1; 356/41; 422/91; 436/136; 436/172
[58] Field of Search ............... 422/91, 52; 250/458.1, 250/459.1; 350/96.34; 356/41; 436/127, 136, 172, 138, 800; 128/633, 634, 635, 664, 665, 666

[56] References Cited

U.S. PATENT DOCUMENTS

| | | | |
|---|---|---|---|
| 4,140,813 | 2/1979 | Hund et al. | 204/290 F |
| 4,174,378 | 11/1979 | Scarpellino, Jr. | 204/47 |
| 4,587,101 | 5/1986 | Marsoner et al. | 436/172 |
| 4,775,514 | 10/1988 | Barnikol et al. | 436/68 |
| 4,810,654 | 3/1989 | Tao | 436/72 |
| 4,810,655 | 3/1989 | Khelil et al. | 128/633 |
| 4,824,789 | 4/1989 | Yafuso et al. | 436/68 |
| 4,861,727 | 8/1989 | Hauenstein et al. | 436/136 |

OTHER PUBLICATIONS

CA 103(20):169703n, "Quenching of Photoexcited State of Hexanuclear $(Mo_6Cl_{14})_2$ by $(IrCl_6)_2$ in Acteonitrile", 1984.
Zietlow, Thomas C. et al., Preparation and Properties of $[((C_6H_5)_3P)_2N]W_6Br_{14}$, Inorg. Chem. 1986, 25, 2198-2201.

Primary Examiner—Robert J. Warden
Assistant Examiner—Timothy M. McMahon

[57] ABSTRACT

A sensor and a method for using the sensor to determine the concentration or partial pressure of oxygen in a fluid media is provided. The sensor includes a light modifying medium containing a luminescent dye which is accessible to oxygen. The luminescent dye contains a hexanuclear core of molybdenum, tungsten or mixtures thereof having 14 coordination sites, wherein each site is occupied by a ligand. The sensor also includes an apparatus capable of transmitting and collecting light to and from the light modifying medium.

48 Claims, 3 Drawing Sheets

APPARATUS AND METHOD FOR MEASURING THE CONCENTRATION OR PARTIAL PRESSURE OF OXYGEN

This Application is a Continuation-in-Part of application Ser. No. 133,594, filed Dec. 14, 1987 now U.S. Pat. No. 4,994,396.

FIELD OF THE INVENTION

The present invention relates to an apparatus and a method for measuring the concentration and/or the partial pressure of oxygen in media, gases such as air, respired air, or the head space above a bioreactor such as a fermentation vessel; liquids such as water in aquariums; body fluids such as blood; and solids such as soils.

BACKGROUND

Optical sensors have been developed for detecting oxygen and which utilize organic or organometallic luminescent species. Such sensors have been disclosed in U.S. Pat. Nos. 3,612,866; 4,321,057; 4,399,099; 4,557,900; and 4,476,870: Lubbers, D. W. and Optiz, N., *Sensors and Actuators*, 4, 641–654, (1983); Lubbers, D. W., et al., *IEEE Transactions on Biomedical Engineering*, BME-33, 117–132, (1986): Fitzgerald, R. V. and Peterson, J. I., *Anal. Chem.* 56, 62–67, (1984); Wolfbeis, D. S., et al., *Mikrochimica Acta*, 153–158, (1984): and Hirschfeld, T.; Miller, H.; and Miller, F., *Optrodes For In Vivo Real Time Monitoring of pCO$_2$ and pO$_2$*, presented at the Pittsburgh Conference, Atlantic City, N.J., March 1986.

While effective, these and other luminescence sensors have the disadvantage of being relatively insensitive to relatively small but significant changes in the concentration or the partial pressure of oxygen in media. Another disadvantage is that the dynamic range over which oxygen can be measured by such sensors is limited, due to their non-linear response at higher oxygen concentrations. And still yet another disadvantage of known sensors is their use in medical applications, where gaseous or volatile anesthetics, such as halothane (bromochlorotrifluoroethane) are employed. These anesthetics will interfere with a luminescence sensor in measuring, for example, oxygen in the blood. The interference by the anesthetic will render such sensors unusable, particularly during critical surgical operations. It would be desirable to obtain a sensor and a method for measuring oxygen concentrations that are more sensitive, have a wider dynamic (i.e. linear) range for measuring oxygen, and are more resistant to interference by anesthetics than are known sensors for measuring oxygen concentrations or partial pressures.

SUMMARY OF THE INVENTION

The present invention is directed to a sensor for determining the concentration or the partial pressure of oxygen comprising:
(a) means for transmitting and collecting light to and from a light modifying medium; and
(b) a light modifying medium containing a luminescent dye dispersed in or upon a matrix and the dye is accessible to oxygen, wherein said luminescent dye contains a hexanuclear core of molybdenum, tungsten, or mixtures thereof having 14 coordination sites, wherein each coordination site is occupied by a ligand.

The present invention is also directed to a composition comprising a luminescent dye dispersed in or upon a matrix wherein the dye is accessible to oxygen, wherein said luminescent dye contains a hexanuclear core of molybdenum, tungsten, or mixtures thereof having 14 coordination sites, wherein each coordination site is occupied by a ligand.

The present invention also is directed to a method for determining the concentration or the partial pressure of oxygen in media, comprising:
(A) inserting a sensor into the medium, wherein the sensor comprises:
  (a) means for transmitting and collecting light to and from a light modifying medium: and
  (b) a light modifying medium comprising a luminescent dye dispersed in or upon a matrix and the dye is accessible to oxygen, wherein said luminescent dye contains a hexanuclear core of molybdenum, tungsten, or mixtures thereof having 14 coordination sites, wherein each coordination site is occupied by a ligand:
(B) transmitting and collecting light to and from said light modifying medium;
(C) measuring the intensity of luminescence collected from the light modifying medium and relating the measured intensity to a known standard to determine the concentration or partial pressure of oxygen present in the medium.

The present invention has the advantage of providing a sensor and a method for measuring oxygen concentrations and partial pressures which are more sensitive to changes in oxygen concentration than by previous known luminescence sensors or methods. Another advantage of the present invention is that it provides a sensor and a method for measuring oxygen concentration which has a wider dynamic and essentially linear range than other known luminescence sensors and methods. And still yet another advantage is that the present invention provides a sensor and a method for measuring oxygen which is substantially less susceptible to interference by volatile anesthetics than other known luminescence sensors or methods.

DETAILED DESCRIPTION OF THE INVENTION

The term "media" means, in its broadest sense, any environment or material in which the concentration or partial pressure of oxygen is to be measured using the sensor or the method of the present invention. Media can be a fluid such as a gas, for example air, respired air or the gas released in a fermentation process or a liquid such as cell culture fluid, or an animal body fluid especially blood, even blood containing an anesthetic in an amount to induce unconsciousness.

The term "hexanuclear core" refers to the 6-membered core of metal atoms, the hexanuclear core having either 6 molybdenum atoms (Mo$_6$), 6 tungsten atoms (W$_6$), or mixtures of the two metals. Such mixtures include but are not limited to combinations such as 5 molybdenum and one tungsten atom (Mo$_5$W); 3 molybdenum atoms and 3 tungsten atoms (Mo$_3$W$_3$); or a molybdenum atom and 5 tungsten atoms (MoW$_5$). Each molybdenum or tungsten atom in the six-membered core has bonded to it a plurality of ligands, described hereinbelow.

The term "coordination site" is defined as the site to which a ligand will bind to the core. The 14 coordination sites are associated with the hexanuclear core and to each site will bind a ligand to the core. Each hexanuclear core of molybdenum, tungsten or mixtures thereof has 14 coordination sites.

The term "ligand" refers to the molecule, ion or atom that is attached to the molybdenum or tungsten atoms in the hexanuclear core. The type of ligand attached to the hexanuclear core can vary greatly, depending upon the desired properties of the luminescent dye. Such ligands include but are not limited to monoanionic ligands such as the halides F, Cl, Br, I: and to CN, SCN, OR, SR, SeR, wherein R is hydrogen, alkyl, aryl or cycloalkyl: anionic nitrogen donating groups such as $NR_2$; and oxygen donating groups such as $O_2CR$, $OP(OR)_2$ and borates, silicates, sulfates and halates wherein R is as defined hereinbefore. Such monoanionic ligands tend to impart a net electronic charge to the luminescent dye which is less than zero or negative.

Other ligands can include neutral species. Such neutral species include oxygen donors such as water, aldehydes, ketones, ethers, esters, alcohols, sulfoxides, sulfones, sulfates, phosphates; and nitrogen donating groups such as ammonia, alkyl or aromatic amines such as primary, secondary or tertiary amines; heterocyclic amines: and sulfur donating groups such as thiols, thioketones, thioacids, thioesters, thioamides, or thioureas, and the like. Such neutral species tend to impart a net electronic charge to the luminescent dye which is zero or neutral.

Other ligands can include cationic species, such as pyridine-4-trimethylammonium, and monoalkylated 4,4'-bipyridinium. Such cationic species tend to impart a net electronic charge to the luminescent dye which is greater than zero or positive.

Other ligands which can impart a combination of positive, negative or neutral charges to the luminescent dye include but are not limited to multicoordinate ligands such as bipyridyl, diketones, dithiols and hydroxyquinones; bridging ligands such as 4,4'-bipyridyl and pyrazine; multivalent ligands such as oxide, sulfide and NR wherein R is as defined hereinbefore; electroactive acceptor ligands such as pyridine, bipyridyl, or monoalkylated bipyridiniums; or charge transfer ligands such as SCN or thiourea or donor ligands such as sulfur containing heterocycles.

The ligand can also be the matrix within or upon which the luminescent dye is dispersed, such as those described hereinbefore. Generally, a matrix which also serves as the ligand will have the requisite oxygen, nitrogen or sulfur donating groups. The matrix can have ligand functional groups which can also act as bridging, solubilizing, or electroactive ligands.

The term "counterion" refers to a molecular species which is in association with the luminescent dye and which electronically balances the negative or positive charge of the luminescent dye. The counterion can be derived from the matrix itself within which the luminescent dye is dispersed.

Thus, the counterion can be cationic such as salts of alkali and alkaline earth metals such as sodium ($Na^+$), potassium ($K^+$), calcium ($Ca^{++}$), magnesium ($Mg^{++}$); ammonium salts corresponding to the formula in which $R_1$, $R_2$, $R_3$ and $R_4$ are sterically feasible and can be identical or different and are each hydrogen, alkyl having 1 to 20 carbon atoms, or phenyl or substituted phenyl which is substituted by up to 5 halogens, or by alkyl groups having 1 to 20 carbon atoms or by alkoxy groups having 1 to 20 carbon atoms. Preferably the cationic counterion is tetrabutyl ammonium.

Also preferred are anionic counterions such as halides including but not limited to chloro, bromo, iodo and fluoro: as well as perchlorates, hexachlorophosphates and tetrafluoroborates.

The term "matrix" means any material which the luminescent dye is dispersed in or upon, so long as the luminescent dye is accessible to oxygen. Thus the matrix can include organic polymeric materials, and inorganic materials, preferably polymeric materials, most preferably organic polymeric materials. Representative polymers include but are not limited to cellulosics such as cellulose acetate, cellulose butyrate, ethyl cellulose: vinyl polymers such as acrylics, polymethyl methacrylate, hydrogels, polyethylene, polystyrene, polyvinyl chloride, polyisobutylene, vinylidene chloride; epoxies such as epoxyimides, epoxyurethane; polyamides and polyamines such as nylons, polyurethanes, polyureas, aramids: polyimides; fluorocarbons such as Nafion ®, (DuPont trademark) polytetrafluoroethylene; polyesters such as allylesters, diallylphthalates, polyethylene terephthalate; silicones (siloxanes) such as polydimethylsiloxane; phosphazenes and functionalized phosphazenes: or copolymers and/or blends of any of the above such as acrylonitrile/butadiene/styrene, and polyvinyl chloride/polyvinyl acetate copolymers; or ionomers.

Typical matrixes which can be used include polymethyl methacrylate (PMMA), polymethylmethacrylate/2-ethylhexyl trimellitate (PMMA/IOTM), polymethylmethacrylate/chlorinated paraffins (PMMA/CP), polyvinyl chloride/di-2-ethylhexyl phthalate (PVC/DOP), polyvinyl chloride/di-2-ethylhexyl adipate (PVC/DiEA), polyvinylacetate/acetyl tributyl citrate (PVA/ATBC), polyvinyl acetate/dibutyl fumarate (PVA/DBF), cellulose acetyl butyrate/di-2-ethylhexyl phthalate (CAB/DOP) and ethyl cellulose/acetyl tributyl citrate (EC/ATBC), most preferably polymethyl methacrylate/2-ethylhexyl diphenyl phosphate (PMMA/EDPP).

Inorganic matrixes which the luminescent dye can be dispersed in or upon include but are not limited to porous glasses, gels, i.e., silica, alumina, zeolites, alumino silicates and alumino phosphates.

Alternatively, the matrix can be the optical waveguide itself or modifications of the waveguide.

Optionally, an additive and preferably, a plasticizer can be added to the polymer material to enhance its permeability to oxygen, improve dispersion of the luminescent dye in the polymer, enhance sensitivity and response time in the light modifying medium, and/or increase flexibility or toughness of the light modifying medium.

Representative plasticizers include but are not limited to isophthalic acid derivatives such as di-(2-ethylhexyl)

isophthalate, dimethyl isophthalate, diphenyl isophthalate; lauric acid derivatives such as methyl laurate; linoleic acid derivative such as methyl linoleate, 75%; maleic acid derivatives such as di-(2-ethylhexyl) maleate, di-n-butyl maleate; mellitates such as tricapryl trimellitate, tri-(2-ethylhexyl) trimellitate, triisodecyl trimellitate, tri-(n-octyl,n-decyl) trimellitate; myristic acid derivatives such as isopropyl myristate; oleic acid derivatives such as butyl oleate, glycerol monooleate, glycerol trioleate, methyl oleate, n-propyl oleate, tetrahydrofurfuryl oleate; palmitic acid derivatives such as isopropyl palmitate, methyl palmitate; paraffin derivatives such as chloroparaffin, 41% Cl, chloroparaffin, 50% Cl, chloroparaffin, 60% Cl, chloroparaffin, 70% Cl; phosphoric acid derivatives such as 2-ethylhexyl diphenyl phosphate (EDDP), isodecyl diphenyl phosphate, t-butylphenyl diphenyl phosphate, tri-butoxyethyl phosphate, tributyl phosphate, tricresyl phosphate, triphenyl phosphate; phthalic acid derivatives such as butyl benzyl phthalate, butyl octyl phthalate, dicapryl phthalate, dicyclohexyl phthalate, di-(2-ethylhexyl) phthalate, diethyl phthalate, dihexyl phthalate, diisobutyl phthalate, diisodecyl phthalate, diisononyl phthalate, diisooctyl phthalate, dimethyl phthalate, ditridecyl phthalate, diundecyl phthalate: ricinoleic acid derivatives such as butyl ricinoleate glyceryl tri(acetyl) ricinoleate), methyl acetyl ricinoleate, methyl ricinoleate, n-butyl acetyl ricinoleate, propylene glycol ricinoleate; sebacic acid derivatives such as dibutyl sebacate, di-(2-ethylhexyl) sebacate, dimethyl sebacate; stearic acid derivatives such as ethylene glycol monostearate, glycerol monostearate, isopropyl isostearate, methyl stearate, n-butyl stearate, propylene glycol monostearate; succinic acid derivatives such as diethyl succinate; sulfonic acid derivatives such as n-ethyl o,p-toluenesulfonamide, o,p-toluenesulfonanamide; adipic acid derivatives such as dicapryl adipate, di-(2-ethylhexyl adipate, di(n-heptyl, n-nonyl) adipate, diisobutyl adipate, diisodecyl adipate, dinomyl adipate, di-(tridecyl) adipate: azelaic acid derivatives such as di-(2-ethylheyl azelate), diisodecyl azelate, diisoctyl azelate, dimethyl azelate, di-n-hexyl azelate: benzoic acid derivatives such as diethylene glycol dibenzoate, dipropylene glycol dibenzoate, polyethylene glycol 200 dibenzoate; citric acid derivatives such as acetyl tri-n-butyl citrate, acetyl triethyl citrate, tri-n-butyl citrate, triethyl citrate: dimer acid derivatives such as bis-(2-hydroxyethyl dimerate): epoxy derivatives such as epoxidized linseed oil, epoxidized soy bean oil, 2-ethylhexyl epoxytallate, n-octyl epoxystereate; fumaric acid derivatives such as dibutyl fumarate; glycerol derivatives such as glycerol triacetate; isobutyrate derivative such as 2,2,4-trimethyl-1,3-pentanediol, diisobutyrate; preferably phosphoric acid derivatives, more preferably 2-ethylhexyl diphenyl phosphate.

The term "luminescent dye" refers to that part of the light modifying medium which modifies the wavelength of the transmitted exciting light, resulting in luminescence (i.e. emitted light) which is collected and whose intensity is modified by the presence of oxygen. The luminescent dye essentially is made of a hexanuclear core of molybdenum, tungsten or mixtures thereof having 14 coordination sites, wherein each coordination site is occupied by a ligand. If the luminescent dye, that is, the core plus the ligand, has a net positive or negative electronic charge, the charge in the luminescent dye will be balanced by a corresponding counterion or counterions.

The light employed in the present invention can be any electromagnetic radiation having a wavelength in the range of about 200 to about 1000 nanometers, including but not limited to ultraviolet, visible and infrared. Preferably, the type of light employed is matched to the specification of the light modifying medium.

The term "dispersed" or "dispersion" means that the luminescent dye is distributed throughout the matrix. Alternatively, the term dispersion can also mean that the luminescent dye is distributed upon a surface of any material which can support the luminescent dye, although it is preferred that the dye be distributed throughout.

Means for transmitting exciting light to the light modifying medium can include but are not limited to optical waveguides such as optical fibers: and optics such as lenses, mirrors and lasers.

Means for collecting light (i.e. luminescence) from the light modifying medium can include but are not limited to optical waveguides such as optical fibers; and optics such as lenses or mirrors. Preferably the means for transmitting and means for collecting light is the same, preferably an optical fiber.

Optionally, and preferably, the optical sensor can have a protective membrane which protects the light modifying medium from deactivating substances, such as liquids, gases or solids. The membrane should be as permeable as possible so that oxygen levels in the light modifying medium can rapidly equilibrate with oxygen levels external to the membrane. Materials which can be used to prepare the membrane include but are not limited to silicone rubber, microporous polyethylene, microporous polypropylene and tetrafluoroethylene (TFE) fluorocarbon polymers such as Teflon ® trademark of the DuPont Corporation.

The concentration or partial pressure of oxygen can be directly determined from the intensity of the collected luminescence after the calibration of the sensor with a known standard. Calibration of the sensor may be based on the quenching of luminescence by oxygen and is described by the equation:

$$1/I = A + (K \times pO_2)$$

wherein I is the intensity of collected luminescence at some partial pressure of oxygen, $pO_2$ is the partial pressure of oxygen in media (or any other measure of oxygen concentration): and A and K are constants which will be functions of the particular conditions of the sensor. Being a linear function of $1/I$ for a given oxygen concentration, the measurement of any two intensities at two different oxygen concentrations or partial pressures will result in the identification of A and K. This will, in turn, allow the determination of oxygen partial pressures up to at least 760 torr of oxygen, from a measure of the collected luminescence intensity at that oxygen partial pressure.

Oxygen standards suitable for relating the measured luminescence intensity can range from an oxygen partial pressure of zero torr (preferably pure nitrogen) to an oxygen partial pressure of 760 torr (preferably pure oxygen). Preferably the standard is an aqueous solution which has been allowed to equilibrate with a gas mixture containing a known partial pressure of oxygen. The range of the partial pressures in the aqueous solution can range from about 0 to about 760 torr, preferably in human blood from about 20 to about 200 torr.

The light modifying medium of luminescent dye, matrix and optionally a plasticizer where an organic polymer matrix is employed, can be prepared by dry blending or mixing the above ingredients, followed by addition of a solvent to ensure adequate dispersion of the luminescent dye in the matrix. Alternatively, the luminescent dye can be pre-dissolved in a solvent and added volumetrically to the matrix. Suitable solvents which can be employed include tetrahydrofuran, toluene, acetone and methylene chloride. The solvent is employed in amounts sufficient to allow working and malleability of the mixture of the solvent/light modifying medium.

The light modifying medium can be applied to any suitable material capable of carrying light of the desired wavelength. Such materials can include but are not limited to plastic, glass, quartz, preferably the material comprising an optical fiber. Generally, the films prepared have a thickness ranging from about 10 microns ($\mu$) to about 1000$\mu$, preferably from about 10 to 100$\mu$. It has been found that no changes in functionality are observed if the light modifying medium is used immediately when dry or allowed to sit overnight. Alternatively, thicker layers can be prepared by applying additional mixture of solvent/light modifying medium over the material to which the light modifying medium has already been spread.

EXAMPLE 1

Preparation of Light Modifying Medium

A luminescent dye-doped plastic matrix containing one percent (%) by weight luminescent dye is prepared by mixing 1 part of $(TBA)_2Mo_6Br_{14}$ (the tetrabutyl ammonium salt of the hexa-molybdenum tetradecyl bromide compound) with 100 parts of a polymer/plasticizer blend. Specifically, 1.8 mg of $(TBA)_2Mo_6Br_{14}$ is mixed with 100 mg of polymethylmethacrylate (PMMA) polymer and 80 mg of 2-ethylhexyl diphenyl phosphate plasticizer (EDPP). To this mix is added 1 to 1.5 ml of tetrahydrofuran solvent (THF). The mixture was heated to 66° C. to help dissolution and remove the amount of solvent to give the final desired viscosity.

About 3 drops of dye/plastic/solvent mixture are applied dropwise to one side of a 3 square centimeter (cm)$^2$ plate made from plastic, glass or quartz, and spread evenly. The plate is allowed to air dry at room temperature.

The plates supporting the light modifying mixture are mounted on aluminum holders and placed inside septa-sealed fluorescence cuvettes. These cuvettes are appropriately configured for front face excitation and emission collection. Such a set-up allowed for the measurement of oxygen concentrations in various gases which are flowed through the cell. Specifically, 420 nanometer (nm) excitation light is used while broad band emission, centered at 670 nm, is detected.

The plate containing a layer of $(TBA)_2Mo_6Br_{14}$ luminescent dye/PMMA-EDDP polymer is calibrated for partial pressures of oxygen ranging from zero millimeters mercury (mm Hg where one mm Hg =one torr) to 760 mm Hg.

EXAMPLE 2

Figure 5:
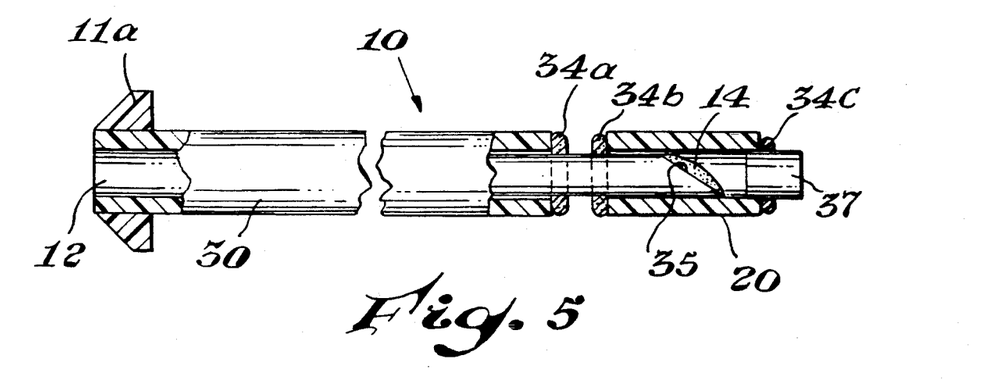
FIG. 5 depicts a cross-sectional view of an embodiment of sensor probe 10 having the same light transmitting and light collecting means as FIG. 4, the modification comprising a geometrical change in the configuration of the distal end of the optical fiber. Also, there is not a mirror plug 36 of FIG. 4 in this embodiment. An optical fiber plug 37 seals the membrane 20.

Performance Characteristics of an Oxygen Sensor Prototype In a Gas Environment A sensor probe 10 was constructed as shown in FIG. 5. A polymeric optical fiber 12 was a 250 micron diameter optical fiber fabricated with an acrylic polymer core (polymethylmethacrylate) sheathed with a fluorine containing polymer having a lower refractive index than the polymer core. The distal end of the optical fiber 12 was cut cross-sectionally at a 30° angle The distal tip was then dipped into a solution of 11.7 mg of the tetrabutyl ammonium salt of hexa-molybdenum tetradecyl bromide, 130 mg poly(methylmethacrylate), and 100 mg of ethylhexyldiphenylphosphate dissolved in 2 ml of tetrahydrofuran. This solution was made by the same method as in Example 1. After the distal tip of the fiber was air dried a dye-dispersed matrix of light modifying medium 14 lay deposited on face 35 of optical fiber 12. The optical fiber was covered with the exception of a short distal portion with size 20 wire gauge tetrafluoroethylene tubing to form a sheath 30 affixed to the optical fiber 12 at glue point 34a. A membrane 20 consisting of 0.042 cm thickness of a silicone rubber medical grade tubing was positioned to surround face 35 and the light modifying medium. The membrane 20 was affixed to optical fiber 12 at glue points 34b and affixed to the optical fiber plug 37 at glue point 34c with urethane adhesive. An optical fiber plug 37 serves to seal membrane 20 at gluepoint 34c. The proximate end of the fiber was connected to an aluminum connector 11a which interfaced to the opto-electronic system of FIG. 1 through a coupler 11 illustrated in FIG. 2.

Figure 1:
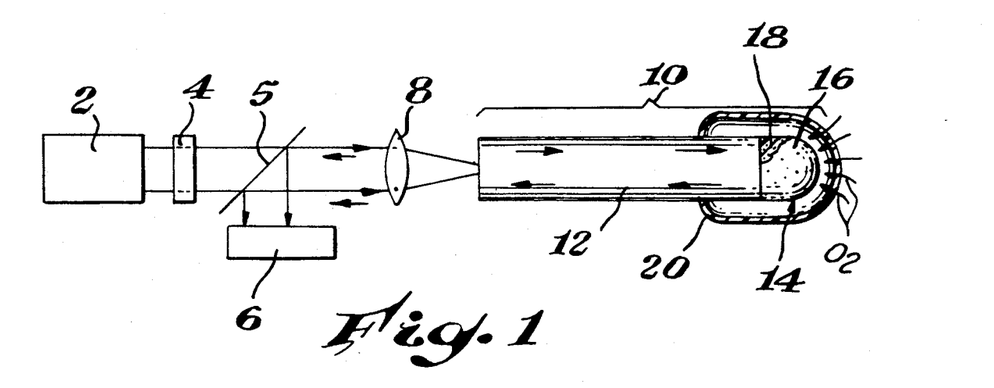
FIG. 1 depicts a schematic representation of a basic system for detecting the partial pressure of oxygen, including optics, detector and sensor.

The opto-electronic system utilized is illustrated in FIG. 1. The light excitation source 2 was a 20 watt quartz-halogen incandescent lamp. The light from the lamp was passed through a bandpass filter 4 and a dichroic beam splitter 5. The light was focused through a lens 8 into the proximate end of the optical fiber 12. The luminescence originating in the light modifying medium 16 is reflected by the dichroic beam splitter 5 into detector 6 which was a silicon photodiode. An additional long-pass filter was placed between the dichroic beam splitter 5 and the detector 6 of FIG. 1 to further exclude stray light. The photodiode output was amplified by a transimpedance amplifier and the resulting voltage was recorded using a digital voltmeter or a chart recorder. It was this signal, in millivolts, that was proportional to the luminescence intensity.

The following procedure was utilized as a calibration protocol for relating the partial pressure of $O_2$ (p$O_2$) to the luminescence intensity (I) of the optical fiber sensor wherein I is inversely proportional to p$O_2$. A calibrating gas stream produced in a PGM 3 precision gas mixer (Utah Medical Products, Inc., Salt Lake City, Utah) was utilized. The gas mixer was capable of delivering either of two gases or a mixture of two gases to a glass tube connected to the calibration gas source. In this case oxygen ($O_2$) and nitrogen ($N_2$) were the two gases that were utilized. The glass tube located at the calibration gas source was blackened on the outside to reduce stray light. The main sources of stray light were the unfiltered light from the incandescent light source of the optoelectronics system, ambient light at the sensor source and ambient light which leaked into the opto-electronics system. The system was corrected for this stray light by adjustments to the gas mixture equilibrating all values to a zero ground point thus subtracting out the effect of the stray light. The gas mixer was set to deliver a gas stream containing variable partial pressure amounts of oxygen and the corresponding luminescence intensities were measured. The luminescence intensity was measured at a p$O_2$ of 0 torr by inserting the sensor probe into the blackened glass tube in the presence of pure nitrogen. The luminescence intensity was measured at a pO$_2$ of 220 torr by inserting the sensor probe into the blackened tube of the gas mixture in an environment of a 220 torr oxygen gas stream.

The stability of the dye-dispersed matrix as a light modifying medium sensitive to pO$_2$ was measured by subjecting the sensor probe to a pO$_2$ environment of 98 torr for a 12 hour period and taking luminescence intensity measurements at various time intervals. The results showed that during the 12 hour period the drift in luminescence intensity varied by less than 2 torr, namely 98 torr ±1 torr pO$_2$.

The accuracy of the sensor was tested by measuring the luminescence intensity as a function of pO$_2$ between the ranges of 0 torr pO$_2$ and 200 torr pO$_2$. The deviation of the data points from the calibration curve was within a range of plus or minus about 0.4 torr.

EXAMPLE 3

Halothane Interference of Oxygen Detection in a Gas Environment

A plate upon which was coated the light modifying medium was prepared according to Example 1. The plate was then calibrated by flowing pure N$_2$ (0 torr O$_2$) and air (160 torr O$_2$) over the coated plate and the luminescence intensity under the conditions of each gas environment was measured. A calibration line was constructed relating the partial pressure of O$_2$, (pO$_2$), to the luminescence intensity, (I), using formula A wherein I=measured luminescence intensity; I(0)=known luminescence intensity at 0 torr pO$_2$; I(160)=known luminescence intensity at 160 torr pO$_2$.

$$pO_2 = \frac{(1/(I) - 1/(I(0))) \times 160}{1/I(160) - 1/I(0)} \qquad A$$

The plate was exposed to a gas mixture containing 4% halothane 1-bromo-1-chloro-2,2,2-trifluoroethane and N$_2$ and the luminescence intensity was recorded. The interference effect of the halothane was manifested by relating the measured luminescence intensity to the torr pO$_2$ required to effect the same luminescence intensity. This is called the equivalent torr pO$_2$ and is found by inserting the measured luminescence intensity of halothane (I) into equation A above to give an equivalent torr pO$_2$. Over a 5 hour period there was an interference in luminescence intensity of the equivalent torr pO$_2$ of less than 0.1 equivalent torr pO$_2$.

BRIEF DESCRIPTION OF THE DRAWINGS

The invention is illustrated by reference to specific embodiments thereof shown in the accompanying drawings, in which.

DETAILED DESCRIPTION OF THE DRAWINGS

Turning to the drawings, in FIG. 1 is shown a source of light 2 equipped with a band pass filter 4. The light excitation of a specific range of wavelengths emitted from light source 2 is passed through a dichroic beam splitter 5, and focused through lens 8 into sensor probe 10. Sensor probe 10 is comprised of a light transmitting and collecting means 12, such as an optical fiber and a light modifying medium 14. Light modifying medium 14 is comprised of luminescent dye 16 dispersed in a matrix 18. Optionally, and preferably light modifying medium 14 is enshrouded or covered with a protective membrane 20 which protects the light modifying medium 14 from deactivating substances.

The light modifying medium 14 modifies the wavelength of the exciting light by emitting luminescence. The luminescence is received by light transmitting and collecting means 12, collimated by lens 8 onto dichroic beam splitter 5 and deflected onto detector 6.

Oxygen (O$_2$) from the external media, i.e., blood, air, etc. penetrates or diffuses through membrane 20 to light modifying medium 14. The oxygen interacts with the light modifying medium 14, altering the intensity of luminescence of the light modifying medium 14. Luminescence from light modifying medium 14 is then emitted back to light detector 6. By measuring the intensity of collected emitted light when calibrated against known standards of oxygen, the partial pressure of oxygen is then determined.

Figure 2:
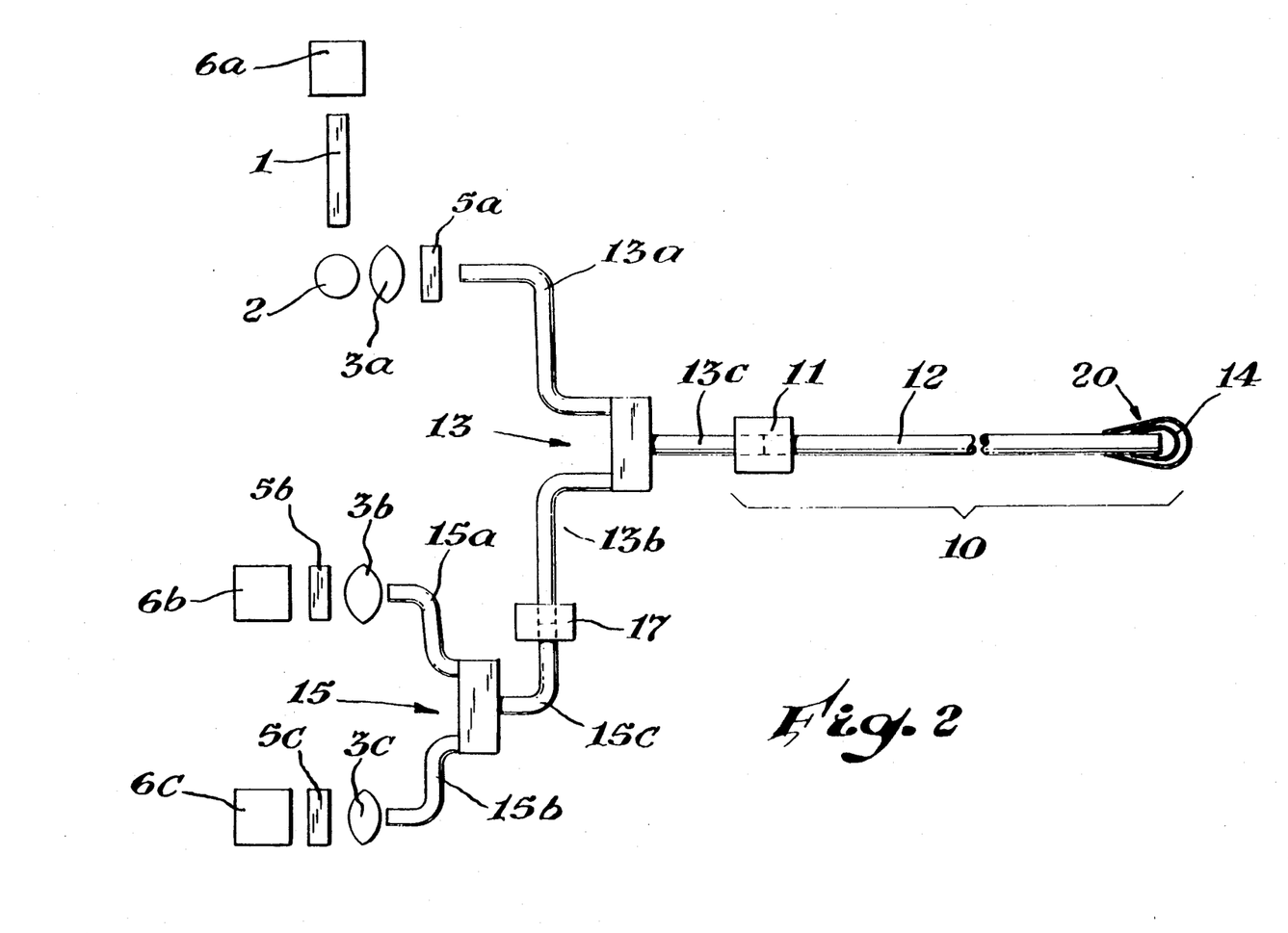
FIG. 2 depicts a schematic representation of a system for detecting oxygen employing multiple detectors.

FIG. 2 shows an apparatus for measuring the partial pressure of oxygen in media and which is somewhat more elaborate than the system shown in FIG. 1.

The source 2 of excitation light yields near ultraviolet (UV) and blue light. The adjoining fiber 1 conducts some portion of the source output to a first detector 6a whose output is used to monitor and/or stabilize the light output from light source 2. The balance of light from source 2 is focused by the lens 3a through the optical filter 5a, whose bandpass preferably approximates the excitation spectrum of the light modifying medium 14, into the optical fiber 13a, which is one pigtail of splitter 13. The single fiber output 13c of splitter 13 is then terminated at coupler 11. Splitter 13 optically interfaces the exciting light from source 2 with sensor 10, and interfaces the collected light from sensor 10 to detectors 6b and 6c.

The sensor fiber 12 is terminated with the light modifying medium 14, which optionally can be surrounded by a selectively permeable membrane 20.

The light modifying medium 14, excited by light originating from source 2 via the path described hereinbefore emits light which is conducted to splitter 13 via the sensor fiber 12 and coupler 11. Splitter 13 diverts a portion of this light via its pigtail 13b into the single pigtail 15c of splitter 15 via coupler 17. Splitter 15 functions to divert a portion of the light returning from the sensor probe 10 through splitter 15 into two detectors 6b and 6c via pigtails 15a and 15b, respectively. Lens 3b collimates one output of splitter 15 through optical filter 5b, whose bandpass preferably approximates the emission spectrum of light modifying medium 14, into detector 6b which converts intensity of this light into a proportional electronic signal.

The second pigtail 15b of splitter 15 is used to divert a portion of the total light returned from sensor probe 10 into a reference detector 6c used to correct for intensity changes in the light emitted from the light modifying medium 14 not caused by changes in the oxygen content of the environment. The reference light could originate from backscattered excitation light from the light modifying medium 14. This light is collimated by lens 3c through the optical filter 5c, whose bandpass preferably approximates that of optical filter 5a into detector 6c, providing an electronic signal proportional to the intensity of the reference light intensity.

The signals from detector 6b and detector 6c are ratioed, with the resulting signal being proportional to the corrected collected intensity of luminescence from light modifying medium 14.

Figure 3:
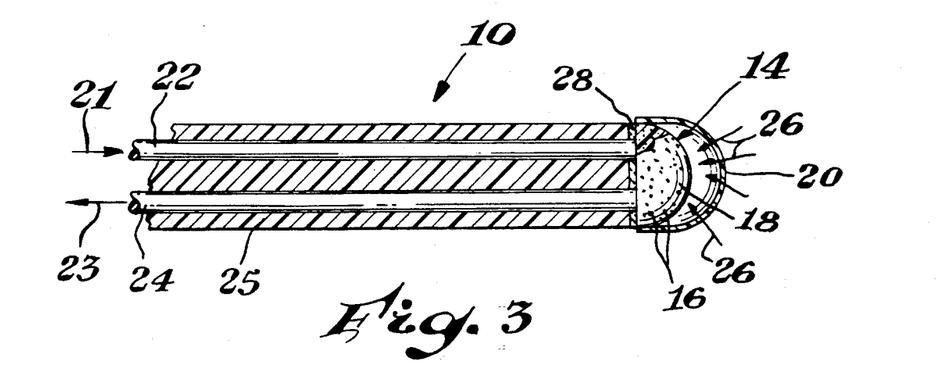
FIG. 3 depicts a cross-sectional view of sensor probe 10 having different light transmitting and light collecting means.

In FIG. 3 is shown in more detail, a cross section of sensor probe 10 employing light transmitting and collecting means in the form of light transmitting optical fiber 22 and light collecting optical fiber 24. Optical fibers 22 and 24 are embedded into suitable substance 25 used to hold the fibers in place. Arrow 21 indicates the direction of exciting light incoming fiber 22 and arrow 23 indicates the direction of light collected or emitted from light modifying medium 14. Optical fibers 22 and 24 adjoin sensor plate 28 upon which light modifying medium 14 is deposited. FIG. 3 also shows protective membrane 20 which enshrouds light modifying medium 14 from deactivating substances. Arrows 26 shows the direction that oxygen travels or diffuses through membrane 20 and ultimately to light modifying medium 14 in order to interact with luminescent dye particles 16 dispersed or embedded in polymer matrix 18.

Figure 4:
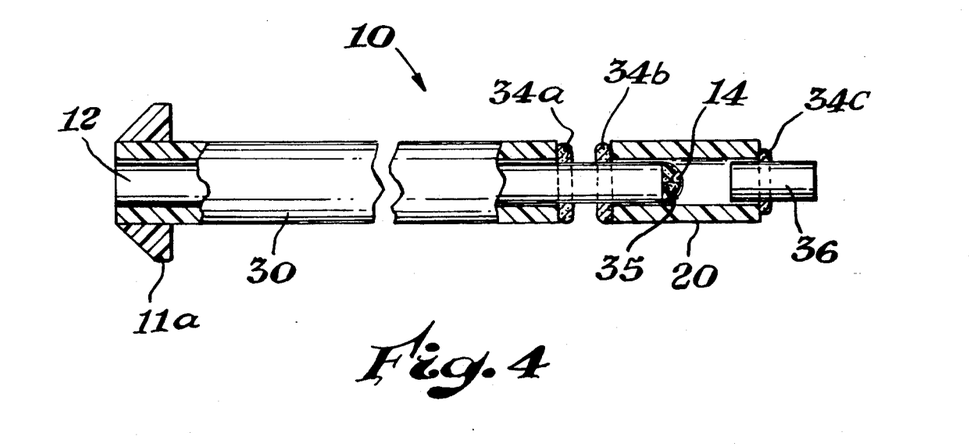
FIG. 4 depicts a cross-sectional view of sensor probe 10 having the same light transmitting and light collecting means.

Turning to FIG. 4 is disclosed sensor probe 10 of an Example 2 embodiment having fiber connector 11a for coupling into a representative coupler 11 as shown in FIG. 2. Sensor probe 10 is made of optical fiber 12 covered by fiber sheath 30 which terminates at glue point 34a. At the end opposite of optical fiber coupler 11a a light modifying medium 14 is deposited on face 35 of optical fiber 12. Membrane 20 surrounds face 35 and light modifying medium 14. Membrane 20 is affixed to fiber 12 at glue point 34b. At the distal end of membrane 20 is affixed a mirrored plug 36 via glue point 34c. Mirror plug 36 serves to reflect a portion of the luminescence from sensing mixture 14 into optical fiber 12.

Turning to FIG. 5, is disclosed another embodiment of sensor probe 10 of Example 4. The modification to the sensor probe of FIG. 4 comprises a geometrical configuration of the distal tip of the optical fiber 12 wherein the light modifying medium 14 is deposited on the tip of the optical fiber face 35 which is cut cross-sectionally at a 30° angle whereas the distal tip face 35 of FIG. 4 is cut cross-sectionally at a 90° angle. Also, there is no mirror plug corresponding to the mirror plug 36 of FIG. 4. The sensor probe 10 has an optical fiber connector 11a for coupling into a representative coupler 11 as shown in FIG. 2. Sensor probe 10 is made of optical fiber 12 covered by fiber sheath 30 which terminates at glue point 34a. Membrane 20 surrounds face 35 with attached light modifying medium 14. Membrane 20 is affixed to fiber 12 at glue points 34b and 34c. An optical fiber plug 37 serves to seal membrane 20 at glue point 34c.

What is claimed is:

1. A sensor useful for determining the concentration or partial pressure of oxygen in a fluid media, the sensor comprising:
    (a) means for transmitting and collecting light to and from a light modifying medium; and
    (b) a light modifying medium containing a luminescent dye accessible to oxygen, wherein said luminescent dye contains a hexanuclear core of molybdenum, tungsten or mixtures thereof having 14 coordination sites, wherein each site is occupied by a ligand.
2. The sensor of claim 1 wherein the means for transmitting and collecting light is an optical waveguide.
3. The sensor of claim 2 wherein the optical waveguide is an optical fiber.
4. The sensor of claim 1 wherein the net electronic charge of the luminescent dye is greater than zero or positive.
5. The sensor of claim 4 wherein the positively charged luminescent dye is balanced by a counterion.
6. The sensor as claimed in claim 1 wherein the net electronic charge of the luminescent dye is less than zero or negative and is balanced by a counterion.
7. The sensor of claim 6 wherein the counterion is tetrabutyl ammonium.
8. The sensor of claim 6 wherein the luminescent dye is $Mo_6Br_{14}^{\ominus\ominus}$ and the counterion is tetrabutyl ammonium.
9. The sensor of claim 1 wherein the luminescent dye contains a hexanuclear core of molybdenum.
10. The sensor of claim 1 wherein the luminescent dye contains a hexanuclear core of tungsten.
11. The sensor of claim 1 wherein the ligand is halide.
12. The sensor of claim 1 wherein the ligand is bromo.
13. The sensor of claim 1 wherein the ligand is iodo.
14. The sensor of claim 1 wherein the luminescent dye is $Mo_6Br_{14}^{\ominus\ominus}$.
15. The sensor of claim 1 wherein the net electronic charge of luminescent dye is zero or neutral.
16. The sensor of claim 1 wherein the luminescent dye is dispersed in a matrix.
17. The sensor of claim 16 wherein the matrix is a polymeric material.
18. The sensor of claim 16 wherein the matrix is an organic polymeric material.
19. The sensor of claim 16 wherein the matrix is polymethylmethacrylate (PMMA).
20. The sensor of claim 16 wherein the matrix is an organic polymer admixed with a plasticizer.
21. The sensor of claim 16 wherein the matrix polymethylmethacrylate admixed with 2-ethylhexyl diphenyl phosphate (EDPP).
22. A method for determining the concentration or partial pressure of oxygen in a media, comprising:
    contacting the media with a light modifying medium comprising a luminescent dye which is accessible to oxygen, wherein said luminescent dye contains a hexanuclear core of molybdenum, tungsten or mixtures thereof each said core having 14 coordination sites, wherein each coordination site is occupied by a ligand;
    (B) transmitting and collecting light to and from said light modifying medium;
    (C) measuring the intensity of luminescence collected from the light modifying medium and using the measured intensity to determine the concentration or partial pressure of oxygen present in the media.

23. The method of claim 22 wherein the luminescent dye contains a hexanuclear core of molybdenum.

24. The method of claim 22 wherein the luminescent dye contains a hexanuclear core of tungsten.

25. The method of claim 22 wherein the ligand is halide.

26. The method of claim 22 wherein the ligand is bromo.

27. The method of claim 22 wherein the ligand is iodo.

28. The method of claim 22 wherein the luminescent dye is $Mo_6Br_{14}^{\ominus\ominus}$.

29. The method of claim 22 wherein the net electronic charge of luminescent dye is zero or neutral.

30. The method of claim 22 wherein the luminescent dye is dispersed in a matrix.

31. The method of claim 30 wherein the matrix is a polymeric material.

32. The method of claim 30 wherein the matrix is an organic polymeric material.

33. The method of claim 30 wherein the matrix is polymethylmethacrylate (PMMA).

34. The method of claim 30 wherein the matrix is an organic polymer admixed with a plasticizer.

35. The method of claim 30 wherein the matrix is polymethylmethacrylate admixed with 2-ethylhexyl diphenyl phosphate (EDPP).

36. The method of claim 27 wherein the net electronic charge of the luminescent dye is greater than zero or positive.

37. The method of claim 36 wherein the positively charged luminescent dye is balanced by a counterion.

38. The method of claim 22 wherein the net electronic charge of the luminescent dye is less than zero or negative.

39. The method of claim 38 wherein the negatively charged luminescent dye is balanced by a counterion.

40. The method of claim 39 wherein the counterion is tetrabutyl ammonium.

41. The method of claim 39 wherein the luminescent dye is $Mo_6Br_{14}^{\ominus\ominus}$ and the counterion is tetrabutyl ammonium.

42. The method of claim 22 wherein the media comprises a fluid containing oxygen having a partial pressure from about 0 torr to about 270 torr.

43. The method of claim 42 wherein the fluid comprises an animal body fluid.

44. The method of claim 42 wherein the fluid comprises animal blood.

45. The method of claim 44 wherein the animal blood contains an anesthetic in an amount to induce an unconscious state.

46. The method of claim 45 wherein the anesthetic is 1-bromo-1-chloro-2,2,2-trifluoroethane.

47. The method of claim 42 wherein the fluid comprises cell culture fluid.

48. The method of claim 42 wherein the fluid comprises a gas in a fermentation vessel.

* * * * *

UNITED STATES PATENT AND TRADEMARK OFFICE
CERTIFICATE OF CORRECTION

PATENT NO. : 5,173,432

DATED : December 22, 1992

INVENTOR(S) : Steven M. Lefkowitz, et al.

It is certified that error appears in the above-identified patent and that said Letters Patent is hereby corrected as shown below:

Column 12, line 51, "21. The sensor of claim 16 wherein the matrix polymethylmethacrylate", should correctly read --21. The sensor of claim 16 wherein the matrix is polyethylmethacrylate--.

Column 12, line 56, "contacting the media with a light modifying medium", should correctly read --(A) contacting the media with a light modifying medium--.

Column 14, line 1, "36. The method of claim 27 wherein the net electronic", should correctly read --36. The method of claim 22 wherein the net electronic--.

Signed and Sealed this

Seventh Day of December, 1993

Attest:

BRUCE LEHMAN

Attesting Officer

Commissioner of Patents and Trademarks